(12) United States Patent
Ohno et al.

(10) Patent No.: US 9,287,506 B2
(45) Date of Patent: Mar. 15, 2016

(54) FULLERENE DERIVATIVE AND PHOTOELECTRIC CONVERSION DEVICE USING SAME

(75) Inventors: Toshinobu Ohno, Osaka (JP); Yuko Takao, Osaka (JP); Kazuyuki Moriwaki, Osaka (JP); Fukashi Matsumoto, Osaka (JP); Takatoshi Ito, Osaka (JP); Toshiyuki Iwai, Osaka (JP); Susumu Yoshikawa, Uji (JP); Takashi Sagawa, Uji (JP); Soichi Uchida, Tokyo (JP); Satoru Ikeda, Tokyo (JP)

(73) Assignees: JX Nippon Oil & Energy Corporation, Tokyo (JP); Osaka Municipal Technical Research Institute, Osaka-shi, Osaka (JP); Kyoto University, Kyoto-shi, Kyoto (JP)

( * ) Notice: Subject to any disclaimer, the term of this patent is extended or adjusted under 35 U.S.C. 154(b) by 222 days.

(21) Appl. No.: 13/980,159

(22) PCT Filed: Jan. 17, 2012

(86) PCT No.: PCT/JP2012/050800
§ 371 (c)(1),
(2), (4) Date: Sep. 30, 2013

(87) PCT Pub. No.: WO2012/099097
PCT Pub. Date: Jul. 26, 2012

(65) Prior Publication Data
US 2014/0014882 A1    Jan. 16, 2014

(30) Foreign Application Priority Data

Jan. 18, 2011 (JP) ................................. 2011-008117

(51) Int. Cl.
| | | |
|---|---|---|
| *H01B 1/04* | (2006.01) | |
| *H01L 51/00* | (2006.01) | |
| *B82Y 30/00* | (2011.01) | |
| *B82Y 10/00* | (2011.01) | |
| *C07C 43/21* | (2006.01) | |
| *H01L 51/42* | (2006.01) | |

(52) U.S. Cl.
CPC ............. *H01L 51/0047* (2013.01); *B82Y 10/00* (2013.01); *C07C 43/21* (2013.01); *C07C 2104/00* (2013.01); *H01L 51/424* (2013.01); *H01L 51/4253* (2013.01); *Y02E 10/549* (2013.01)

(58) Field of Classification Search
CPC ....... H01B 1/04; H01L 51/0047; H01L 51/00
USPC ........... 252/500–511; 136/263; 977/734, 737, 977/740
See application file for complete search history.

(56) References Cited

U.S. PATENT DOCUMENTS

2006/0159611 A1 * 7/2006 Hummelen et al. ...... 423/445 B
2010/0127244 A1 * 5/2010 Kronholm et al. ............. 257/40
2011/0313189 A1 * 12/2011 Varotto et al. ................ 560/102

FOREIGN PATENT DOCUMENTS

| JP | 2002154992 A1 * | 5/2002 | .............. C07C 13/62 |
|---|---|---|---|
| JP | 2005-255591 A | 9/2005 | |
| JP | 2009-054936 A | 3/2009 | |
| JP | 2009-057356 A | 3/2009 | |
| JP | 2011-124470 A | 6/2011 | |

OTHER PUBLICATIONS

Tzirakis et al. ("Hydroxyalkylation of [60]fullerene: free radical addition of alcohols to C60." ChemComm, 46, pp. 8228-8230, 2010).*
Okamura et al. ("Synthesis of 1,4-Dipolystyryldihydro[60]fullerenes by Using 2,2,6,6-Tetramethyl-1-polystyroxypiperidine as a Radical Source." Macrom, 30, pp. 5279-5284, 1997).*
Int'l Search Report issued Apr. 3, 2012 in Int'l Application No. PCT/JP2012/050800.
Nakamura et al, "Mono- and Penta-Addition of Enol Silyl Ethers to [60]Fullerene," Organic Letters, vol. 10, No. 21, pp. 4923-4926 (2008).
Mori et al, "A Bench-Stable Pd Catalyst for the Hydroarylation of Fullerene with Boronic Acids," Organic Letters, vol. 10, No. 20, pp. 4609-4612 (2008).

(Continued)

*Primary Examiner* — Tri V Nguyen
(74) *Attorney, Agent, or Firm* — Panitch Schwarze Belisario & Nadel LLP

(57) ABSTRACT

The present invention provides a fullerene derivative having an electron donating group adjacent to the fullerene nucleus, represented by formula (I) which exhibits a high LUMO energy and a high open circuit voltage based thereon and which is highly compatible with polymers and excellent in charge mobility and charge separation ability:

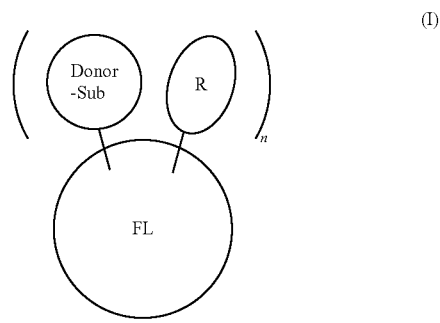

wherein the encircled FL represents fullerene $C_{60}$ or $C_{70}$, Donor-Sub represents a substituent having at least one electron donating substituent atom located at a position apart from the fullerene nucleus by two bonds, R is hydrogen, Donor-Sub, an alkyl, cycloalkyl, alkoxy, alkoxy-substituted alkyl, alkoxy-substituted alkoxy, alkylthio-substituted alkoxy, alkylthio, alkylthio-substituted alkylthio, or alkoxy-substituted alkylthio group, having a total carbon atoms of 1 or more and 20 or fewer, or a benzyl or phenyl group, and n is an integer of 1 to 10.

4 Claims, No Drawings

(56) References Cited

OTHER PUBLICATIONS

Matsuo et al, "Synthesis of Imino[60]fullerenes Using Nitriles and Trimethylsilylmethyl Triflate," Organic Letters, vol. 11, No. 18, pp. 4192-4194 (2009).

Nambo et al, "Aziridinofullerene: A Versatile Platform for Functionalized Fullerenes," Journal of the American Chemical Society, vol. 133, pp. 2402-2405 (2011).

Varotto et al, "1,4-Fullerene Derivatives: Tuning the Properties of the Electron Transporting Layer in Bulk-Heterojunction Solar Cells," Angewandte Chemie International Edition, vol. 50, pp. 5166-5169 (2011).

Reyes-Reyes et al, "High-efficiency photovoltaic devices based on annealed poly(3-hexylthiophene) and 1-(3-methoxycarbonyl)-propyl-1-phenyl-(6,6)C61 blends," Applied Physics Letters, vol. 87, No. 083506, pp. 1-3 (2005).

Ma et al, "Thermally Stable, Efficient Polymer Solar Cells with Nanoscale Control of the Interpenetrating Network Morphology," Advanced Functional Materials, vol. 15, pp. 1617-1622 (2005).

Scharber et al, "Design Rules for Donors in Bulk-Heterojunction Solar Cells—Towards 10% Energy-Conversion Efficiency," Advanced Materials, vol. 18, pp. 789-794 (2006).

Lenes et al, "Fullerene Bisadducts for Enhanced Open-Circuit Voltages and Efficiencies in Polymer Solar Cells," Advanced Materials, vol. 20, pp. 2116-2119 (2008).

Riedel et al, "Polymer solar cells with novel fullerene-based acceptor," Thin Solid Films, vol. 43, pp. 451-452 (2004).

Kooistra et al, "Increasing the Open Circuit Voltage of Bulk-Heterojunction Solar Cells by Raising the LUMO Level of the Acceptor," Organic Letters, vol. 9, No. 4, pp. 551-554 (2007).

\* cited by examiner

FULLERENE DERIVATIVE AND PHOTOELECTRIC CONVERSION DEVICE USING SAME

CROSS-REFERENCE TO RELATED APPLICATION

This application is a Section 371 of International Application No. PCT/JP2012/050800, filed Jan. 17, 2012, which was published in the Japanese language on Jul. 26, 2012 under International Publication No. WO 2012/099097 A1, and the disclosure of which is incorporated herein by reference.

TECHNICAL FIELD

The present invention relates to fullerene derivatives and photoelectric conversion device containing the same.

BACKGROUND ART

The organic thin film solar cell is an all solid type thin film solar cell containing an organic semiconductor and thus has been expected to be large in area and produced by an inexpensive manner, as well as light in weight and rich in flexibility. However, a significant increase in the conversion efficiency of the organic thin film solar cell has become an important issue towards the practical realization of the cell, and as the result, researches and development therefor have been vigorously carried out around Europe and the United States.

The fullerene derivative is an organic semiconductor material that is high in electron accepting properties and has been expected to be applied to an organic photoelectric conversion device (organic solar cells, light sensors). A methanofullerene wherein phenyl and butyric acid ester groups are cross-linked with methylene (phenyl-$C_{61}$-butyric acid methyl ester; PCBM) is a widely known fullerene derivative for an organic thin film solar cell, and an improvement in energy conversion efficiency by 5 percent was achieved by an organic thin film solar cell of bulk heterojunction structure comprising a mixed active layer of the PCBM and a conjugated polymer, i.e., poly(3-hexylthiophene: P3HT) (see Non-Patent Literatures 1 and 2).

The energy conversion efficiency is represented by the formula "conversion efficiency ($\eta$)=open circuit voltage ($V_{OC}$)×short circuit current ($J_{SC}$)×fill factor (FF)".

As apparent from the formula, an increase in open circuit voltage contributes significantly to an increase in conversion efficiency. Furthermore, it is known that the open circuit voltage correlates strongly to the energy difference between the HOMO (highest occupied molecular orbital) of a donor and the LUMO (lowest unoccupied molecular orbital) of an acceptor (Non-Patent Literature 3), and thus an increase in the LUMO energy of an acceptor material leads to an increase in open circuit voltage. Specifically, Blom et al have reported that bismethanofullerene (bisPCBM) where two phenyl butyric acid ester groups were substituted was increased in LUMO energy by about 100 meV compared with PCBM (by first reduction potential measurement) and thus was increased in open circuit voltage by 0.15 V and had 1.2 time of photoelectric conversion efficiency (Non-Patent Literature 4).

Non-Patent Literature 5 is an example which refers to the LUMO energy level of an acceptor material and has designed an acceptor having a higher LUMO energy than PCBM, but exhibited an open circuit voltage of 0.65 V when formed into a device with P3HT, which open circuit voltage cannot be regarded as a significant improvement.

Meanwhile, in Non-Patent Literature 6, a study was carried out about the correlation of open circuit voltages of various methanofullerene derivatives produced by introducing substituents into the phenyl group of PCBM, but these compounds have methanofullerene derivative structures where the substituents are substituted for the fullerene nucleus via a methylene bridge and thus the effect of the substituents is indirect with respect to the fullerene nucleus. There is, therefore, a certain limit to enhance the LUMO energy.

As described above, these reports are generally insufficient as guidelines to obtain higher open circuit voltage and thus insufficient to solve the problems.

CITATION LIST

Non-Patent Literature

Non-Patent Literature 1: "Applied Physics Letters" by M. R-Reyes, K. Kim, D. L. Carroll, vol. 87, 083506, 2005, Non-Patent Literature 2: "Advanced Functional Material" by W. Ma, C. Yang, X. Gong, K. Lee, A. J. Heeger, vol. 15, p. 1617-1622, 2005

Non-Patent Literature 3: "Advanced Material" by M. C. Scharber, D. Muhlbacher, M. Koppe, P. Denk, C. Waldauf, A. J. Heeger, C. J. Brabec, vol. 18, p. 789-794, 2006

Non-Patent Literature 4: "Advanced Material" by M. Lenes, G. A. H. Wetzelaer, F. B. Kooistra, S. C. Veenstra, J. C. Hummelen, P.W.M. Blom, vol. 20, p. 2116-2119, 2008, Non-Patent Literature 5: "Thin Solid Films" by I. Riedel, N. Martin, F. Giacalone, J. L. Segura, D. Chirvase, J. Parisi, V. Dyakonov, vol. 43, p. 451-452, 2004, Non-Patent Literature 6: "Organic Letters" by F. B. Kooistra, J. Knol, F. Kastenberg, L. M. Popescu, W. J. H. Verhees, J. M. Kroon, J. C. Hummelen, vol. 9, p. 551-554, 2007

SUMMARY OF INVENTION

Technical Problem

As the results of extensive research and study in view of the above-described problems, the inventors of the present invention have succeeded in developing a novel fullerene derivative providing a high LUMO energy by introducing substituents directly into a fullerene without via a methylene bridge. The use of the novel fullerene derivative according to the present invention can produce a photoelectric conversion device exhibiting a high open circuit voltage.

Solution to Problem

The present invention relates to a fullerene derivative represented by formula (I).

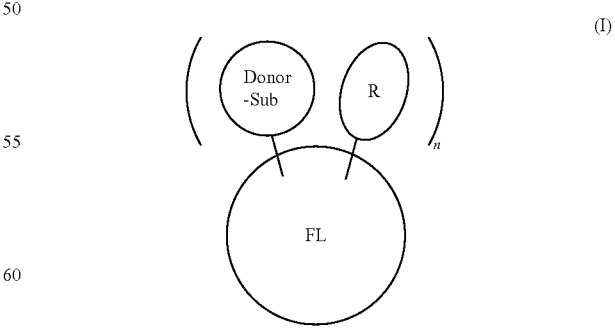

(I)

In formula (I), the encircled FL represents fullerene $C_{60}$ or $C_{70}$, Donor-Sub represents a substituent having at least one electron donating substituent atom located at a position apart from the fullerene nucleus by two bonds, R is hydrogen, Donor-Sub, an alkyl, cycloalkyl, alkoxy, alkoxy-substituted alkyl, alkoxy-substituted alkoxy, alkylthio-substituted alkoxy, alkylthio, alkylthio-substituted alkylthio, or alkoxy-substituted alkylthio group, having a total carbon atoms of 1 or more and 20 or fewer, or a benzyl or phenyl group, and n is an integer of 1 to 10.

The present invention also relates to the forgoing fullerene derivative having a first reduction potential of 1160 mV or higher.

The present invention also relates to a photoelectric conversion device having a heterojunction layer comprising a p type conjugate polymer having electron donating properties and an n type fullerene derivative, wherein the foregoing fullerene derivative is used in a photoelectric conversion layer.

Advantageous Effects of Invention

Since the fullerene derivative of the present invention can be synthesized at a high yield and has a high LUMO energy, it can provide an organic thin film solar cell exhibiting a high open circuit voltage and therefore is extremely useful as an acceptor material for an organic thin film solar cell.

DESCRIPTION OF EMBODIMENTS

The present invention will be described in detail below.

The fullerene derivative of the present invention is represented by formula (I) and characterized by having an electron donating structure (hereinafter referred to as "Donor-Sub") adjacent to the fullerene nucleus.

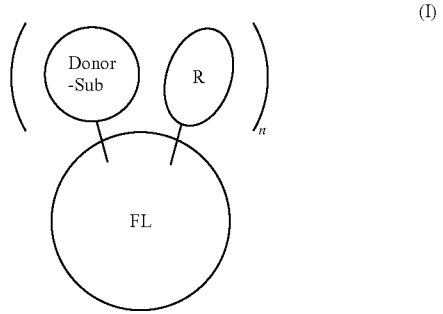

(I)

In formula (I), the encircled FL represents fullerene $C_{60}$ or $C_{70}$.

Donor-Sub represents a monovalent substituent having an aromatic ring or heterocyclic ring with at least one electron donating substituting atom located at a position apart from the fullerene nucleus by two bonds, and R is hydrogen, Donor-Sub, an alkyl, cycloalkyl, alkoxy, alkoxy-substituted alkyl, alkoxy-substituted alkoxy, alkylthio-substituted alkoxy, alkylthio, alkylthio-substituted alkylthio, or alkoxy-substituted alkylthio group, having a total carbon atoms of 1 or more and 20 or fewer, or a benzyl or phenyl group. No particular limitation is imposed on the number of paired Donor-Sub and substituent R. However, n is an integer of 1 to 10, preferably 1 to 6.

Examples of Donor-Sub in formula (I) include those having the following structures.

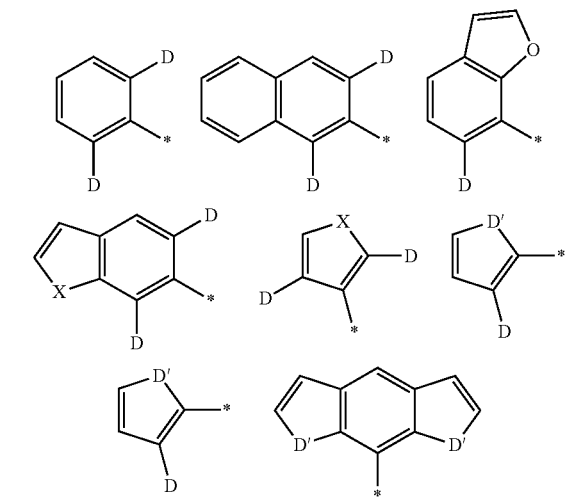

$D = OR^1, NR^1{}_2, SR^1$
$D' = O, S$

In the above formulas, $R^1$ is an alkyl, cycloalkyl, alkoxy, alkoxy-substituted alkyl, alkoxy-substituted alkoxy, alkylthio-substituted alkoxy, alkylthio, alkylthio-substituted alkylthio, or alkoxy-substituted alkylthio group, having a total carbon atoms of 1 or more and 20 or fewer, or a benzyl or phenyl group and may contain an unsaturated bond or a branched structure in part of the bonds. Specific examples of $R^1$ include methyl, ethyl, propyl, butyl, pentyl, hexyl, heptyl, octyl, nonyl, decyl and isomers thereof, methoxymethyl, ethoxymethyl, ethoxyethyl, methoxyethyl, methoxyethoxyethyl, and ethoxyethoxyethyl groups.

Specific examples of these Donor-Subs include the followings but are not limited thereto. In the following formulas, Me is methyl and Et is ethyl.

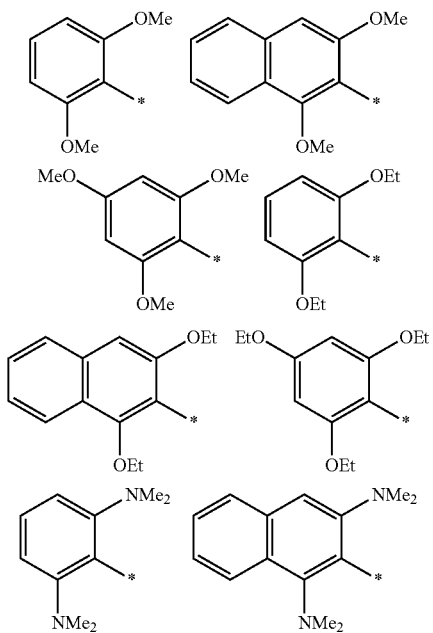

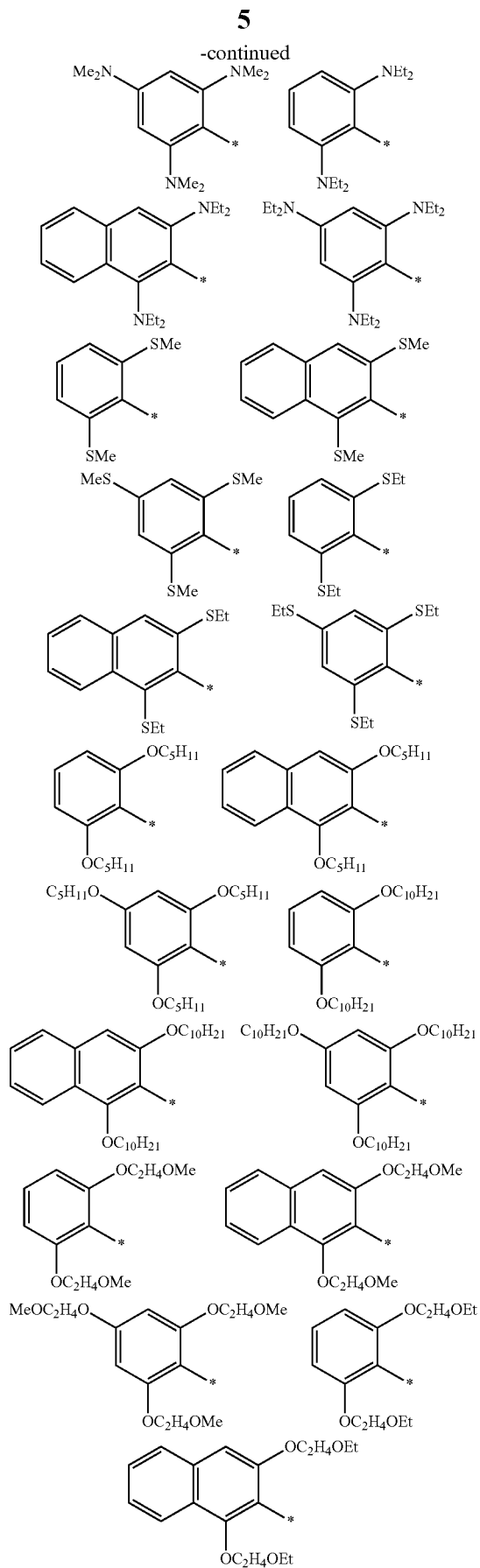
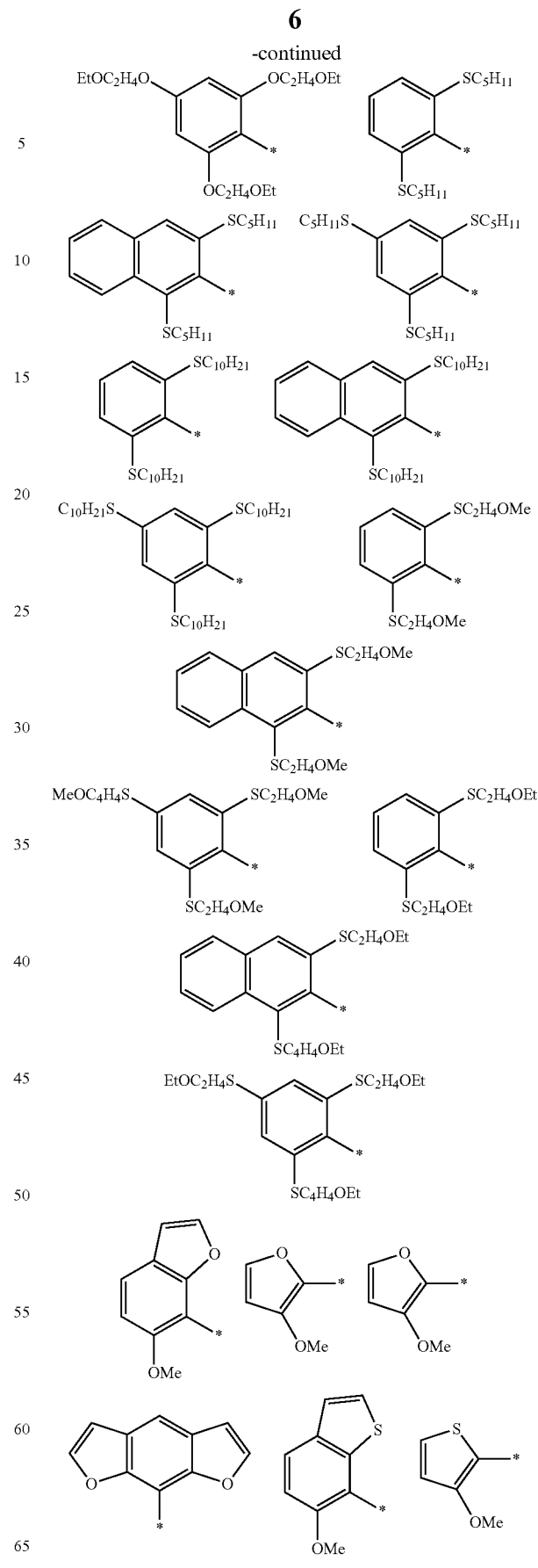

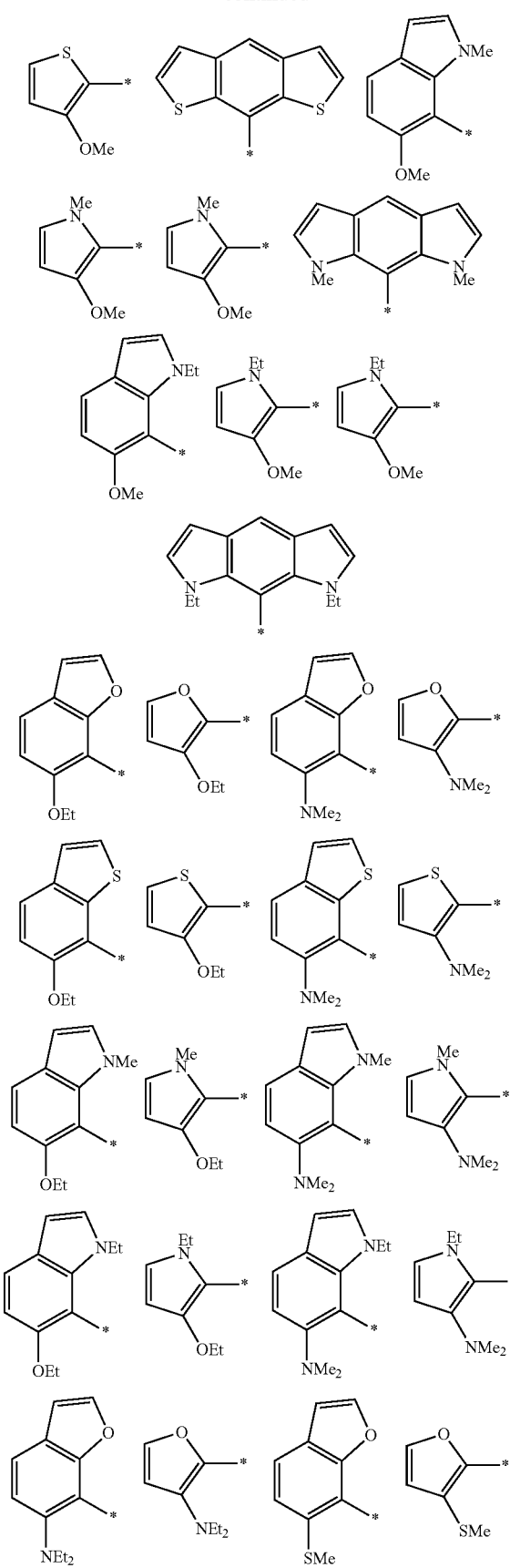
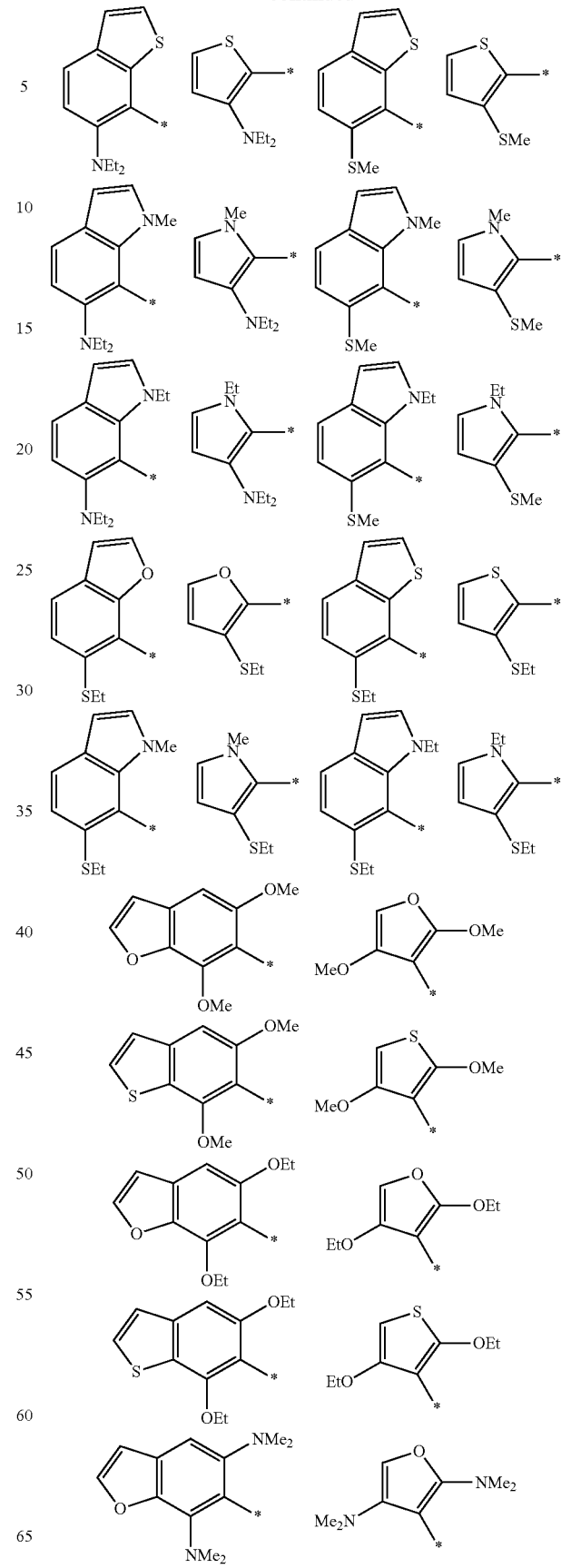

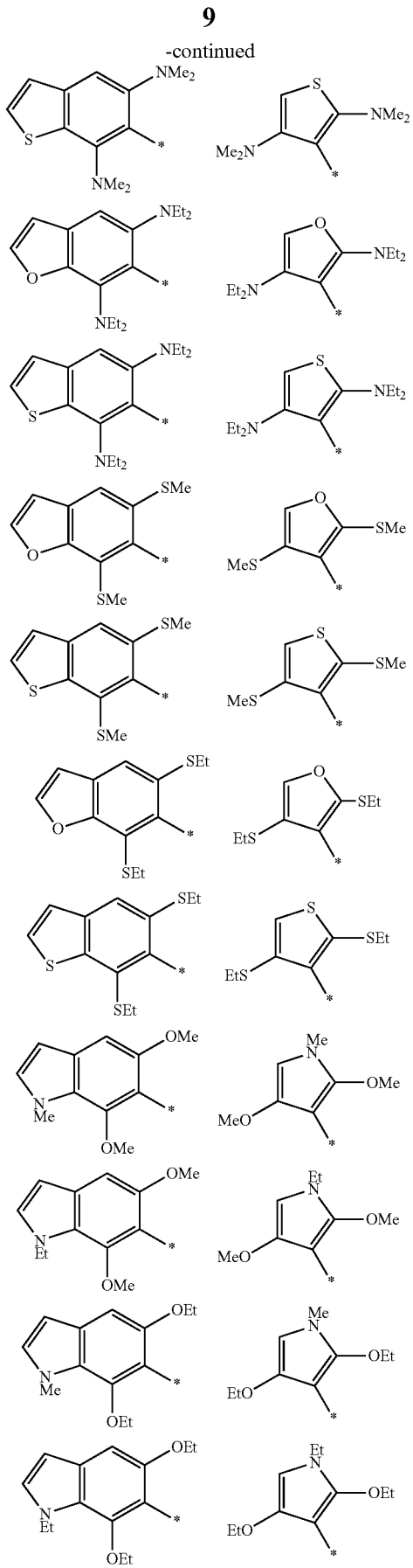
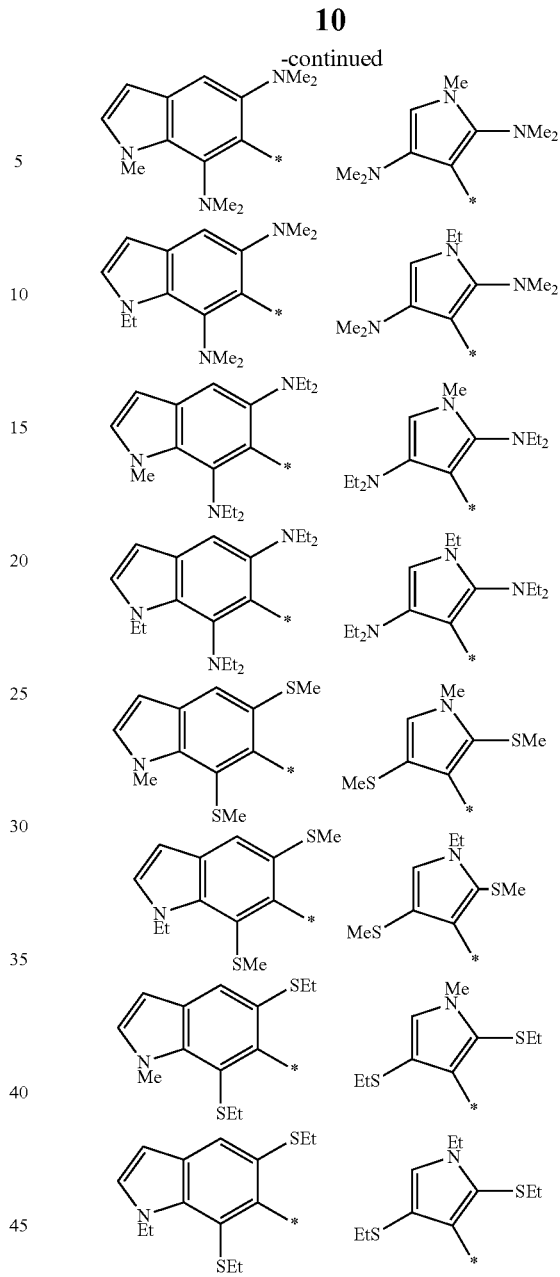

[Method for Producing Fullerene Derivative]

A method for synthesizing the fullerene derivative of the present invention will be described but is not limited thereto. Boronic acids (corresponding to 1a, 2a, 3a in Examples below) and fullerene $C_{60}$, which are precursors of the intended fullerene are heated in the presence of a rhodium catalyst in o-dichlorobenzene/water at a temperature of 60 to 100° C. for one to 12 hours (see "Chem. Soc." vol. 129, p. 8080-8081, 2007 by M. Nambo, R. Noyori, K. Itami, J. Am.) thereby producing the intended fullerene derivative. Furthermore, the resulting fullerene derivative is reacted with an organic halide (corresponding to 4, 5, 6 in Examples below) in o-dichlorobenzene/benzonitrile to which potassium-tert-butoxide has been added, at room temperature to 150° C. thereby producing a fullerene derivative having two different kinds of substituents. Alternatively, an oxidized fullerene $C_{60}O$ is reacted with a benzene derivative (corresponding to 7a, 8a in Examples below) in the presence of Lewis acid in o-dichlorobenzene at 0° C. thereby producing a fullerene derivative having two Donor-subs.

[Evaluation of LUMO Energy of Fullerene Derivative]

The fullerene derivative of the present invention exhibits a higher LUMO energy level than the conventional fullerene derivative (PCBM). It is known that as the LUMO energy is higher, the open circuit voltage tends to be high. The LUMO energy of a fullerene derivative may be generally evaluated by determining and/or comparing the first reduction potential measured with cyclic voltammetry. That is, it is suggested that a fullerene derivative with a higher first reduction potential be higher in LUMO energy level. For example, the first reduction potential may be measured by dissolving a fullerene derivative in an o-dichlorobenzene solution containing a tetrabutylammonium perchloric acid salt and then measuring it by potentiostat/galvanostat. The first reduction potential can be obtained as an average value of the first reduction peak and the oxidation peak thereof, using the oxidation/reduction potential (Fc/Fc$^+$) of a ferrocene as the internal reference. The fullerene derivative of the present invention has a feature that it exhibits a higher first reduction potential than at least PCBM and exhibits a reduction potential of at least 1160 mV (vs Fc/Fc$^+$) or higher.

[Organic Photoelectric Conversion Device]

Next, a description will be given of a photoelectric conversion device (organic photoelectric conversion device) produced using the fullerene derivative of the present invention. For example, the photoelectric conversion device of the present invention may be a heterojunction type device having a photoelectric conversion layer formed by laminating or mixing the fullerene derivative used as an electron transport material with a suitable hole transport material. Alternatively, a layer may be formed using only the fullerene derivative of the present invention. The hole transport material is desirously a low molecular weight dye or a polymer compound.

The structure of the heterojunction type electron device of the present invention may be a structure having a photoelectric conversion layer formed by the fullerene derivative of the present invention and a hole transport material between an electrically conductive electrode substrate at least one of which surface is transparent or translucent and a counter electrode.

During the operation of the organic photoelectric conversion device, light energy entered through a transparent/translucent electrode is absorbed by a photoelectric conversion layer formed of an organic semiconductor material and excitons are generated. The exciton migrates to the heterojunction interface between the electron transport material and the hole transport material, and then is separated to an electron and a hole thereby generating charges (electron and hole). The charge thus generated migrates to the electrode and is externally withdrawn in the form of electrical energy.

The hole transport material used in the organic photoelectric conversion device may be a hole transport polymer such as polyphenylene vinylene, polythiophene, polypyrrole, polyaniline, or polycarbazole. Among these compounds, the hole transport material is preferably a compound having a relatively high mobility such as thiophene-based polymers or copolymers of thiophenes and other compounds with conjugate structures.

The photoelectric conversion layer may be produced by a method where the fullerene derivative of the present invention and the above-described hole transport material are dissolved in a solvent and then coated on a substrate. The solvent may be any solvent if it can dissolve both the fullerene derivative and hole transport material. Examples of such a solvent include toluene, xylene, chloroform, dichloromethane, tetrahydrofuran, carbon tetrachloride, chlorobenzene, dichlorobenzene, trichlorobenzene, and carbon disulfide. The solution may be coated on a surface of a substrate surface by a method such as casting, spin coating, spray coating, and bar coating. The photoelectric conversion layer is finally formed by evaporating the solvent.

The transparent electrically conductive substrate is generally produced by laminating a transparent electrode layer over a transparent substrate. No particular limitation is imposed on the transparent substrate, which may be glass, plastic resin material, and silicon. Examples of the resin material include polyester, polyamide, polysulfone, polyethersulfone, polyether ether ketone, polycarbonate, polyimide, polymethylmethacrylate, and polystyrene.

The transparent electrically conductive film forming the transparent electrode of electrically conductive layer may be a metal film of gold, silver, chromium, copper, or tungsten or an electrically conductive film of a metal oxide. Examples of suitable metal oxide film include films produced by doping a trace amount of a different metal element to tin oxide or zinc oxide, such as indium tin oxide (ITO) or NESA. The film thickness is usually from 1 nm to 50 μm, preferably from 10 nm to 10 μm.

The counter electrode may be a metal such as gold, platinum, silver, copper, aluminum, magnesium, lithium, and potassium or a carbon electrode. The counter electrode may be produced by vacuum deposition, electron beam vacuum deposition, or sputtering.

Before forming the counter electrode metal layer, a buffer layer may be additionally formed between the photoelectric conversion layer and the counter electrode metal layer. No particular limitation is imposed on the material of the buffer layer, which may, however, be an organic such as phenanthroline or bathocuproin, an inorganic compound or inorganic oxide such as lithium fluoride or TiOx.

Photoelectric conversion devices can be evaluated by attaching terminals to the transparent electrode and counter electrode and measuring the change in current value when light is irradiated or not.

EXAMPLES

The present invention will be described in more details with reference to the following examples but is not limited thereto.

Example 1

Synthesis of Fullerene Derivative 1b

Fullerene derivative 1b (BDP-H) was synthesized in the following manner.

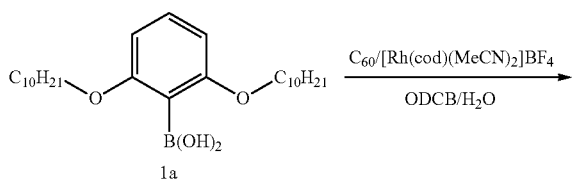

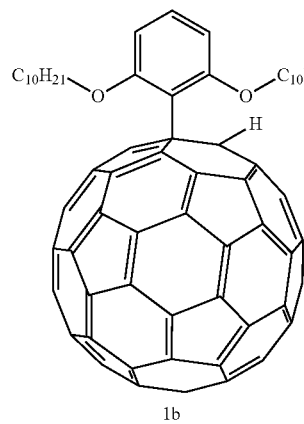

1b

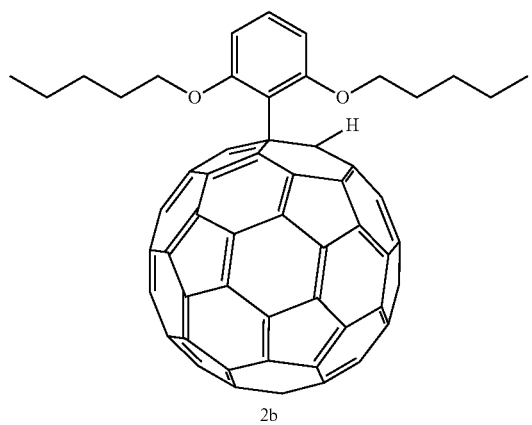

2b

Into a 100 mL eggplant flask were put 362 mg of a boronic acid compound 1a, 500 mg of C$_{60}$ and 26 mg of catalyst [Rh(cod)(MeCN)$_2$]BF$_4$ (cod represents 1,5-cyclooctadiene), to which 50 mL of o-dichlorobenzene (ODCB) and 12.5 mL of water were added under an argon gas atmosphere followed by stirring at 60° C. for two hours. After completion of the reaction, insolubles were filtered out and the solvent was removed under reduced pressure. The resulting product was separated and refined by recycle preparative column chromatography (toluene solvent) thereby producing 521 mg of 1b (yield 67%). The resulting product was confirmed with a high-performance liquid chromatography and identified with $^1$H-NMR, $^{13}$C-NMR, and MALDI-TOF-MS.

[Analyzed Data]

$^1$H-NMR (270 MHz; CDCl$_3$) δ7.48 (t, 1H, 8.4 Hz), 6.95 (d, 2H, 8.6 Hz), 6.80 (s, 1H), 4.30 (br, 4H), 1.86-1.84 (m, 4H), 1.22 (br, 26H), 0.84 (t, 6H, 6.4 Hz); $^{13}$C-NMR (67.8 MHz; CDCl$_3$) δ158.64, 156.46, 155.06, 147.32, 146.44, 146.32, 146.22, 146.15, 146.06, 146.05, 145.41, 145.34, 145.15, 144.98, 144.81, 144.78, 143.42, 142.59, 142.51, 142.29, 142.00, 141.75, 141.57, 141.52, 140.07, 139.23, 137.79, 135.51, 129.62 (CH), 122.99, 106.43 (CH), 70.07 (OCH$_2$), 64.01, 63.28 (CH), 31.86 (CH$_2$), 29.66 (CH$_2$), 29.56 (CH$_2$), 29.3 (CH$_2$), 29.26 (CH$_2$), 26.8 (CH$_2$), 22.66 (CH$_2$), 14.11 (CH$_3$); MALDI-TOF-MS 1110.4[M]$^+$.

Example 2

Synthesis of Fullerene Derivative 2b

Fullerene derivative 2b (BPP-H) was synthesized in the following manner.

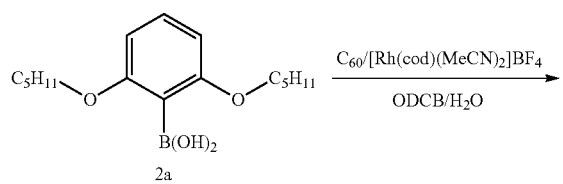

2a

Into a 200 mL eggplant flask were put 219 mg of a boronic acid compound 2a, 488 mg of C$_{60}$ and 26 mg of catalyst [Rh(cod)(MeCN)$_2$]BF$_4$, to which 60 mL of o-dichlorobenzene and 15 mL of water were then added under an argon gas atmosphere, followed by stirring at 60° C. for 4 hours. After completion of the reaction, insolubles were filtered out and the solvent was removed under reduced pressure. The resulting product was separated and refined by recycle preparative column chromatography (toluene solvent) thereby producing 508 mg of 2b (yield 77%). The resulting product was confirmed with a high-performance liquid chromatography and identified with $^1$H-NMR, $^{13}$C-NMR, and MALDI-TOF-MS.

[Analyzed Data]

$^1$H-NMR (300 MHz; CDCl$_3$/CS$_2$) δ7.44 (t, 1H, 8.3 Hz), 6.90 (d, 2H, 8.4 Hz), 6.76 (s, 1H), 4.28 (br, 4H), 1.88-1.83 (m, 4H), 1.49-1.31 (m, 12H), 0.89 (t, 6H, 7.2 Hz); $^{13}$C-NMR (75 MHz; CDCl$_3$/CS$_2$) δ158.47, 156.24, 154.85, 147.38, 147.19, 147.14, 146.27, 146.20, 146.06, 145.95, 145.92, 145.29, 145.27, 145.03, 144.88, 144.70, 144.67, 143.35, 142.99, 142.49, 142.41, 142.18, 141.89, 141.61, 141.47, 141.42, 139.81, 139.13, 137.66, 135.38, 129.56 (CH), 122.77, 106.33 (CH), 69.91 (OCH$_2$), 63.83, 63.19 (CH), 28.97 (CH$_2$), 28.85 (CH$_2$), 22.74 (CH$_2$), 26.8 (CH$_2$), 22.66 (CH$_2$), 14.14 (CH$_3$); MALDI-TOF-MS 971.2[M]$^+$.

Example 3

Synthesis of Fullerene Derivative 3b

Fullerene derivative 3b (BMEP-H) was synthesized in the following manner.

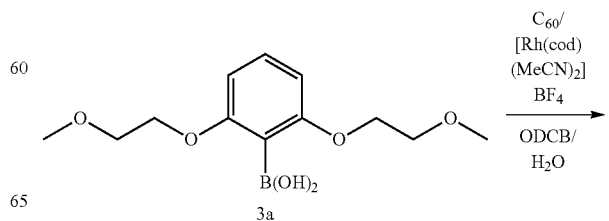

3a

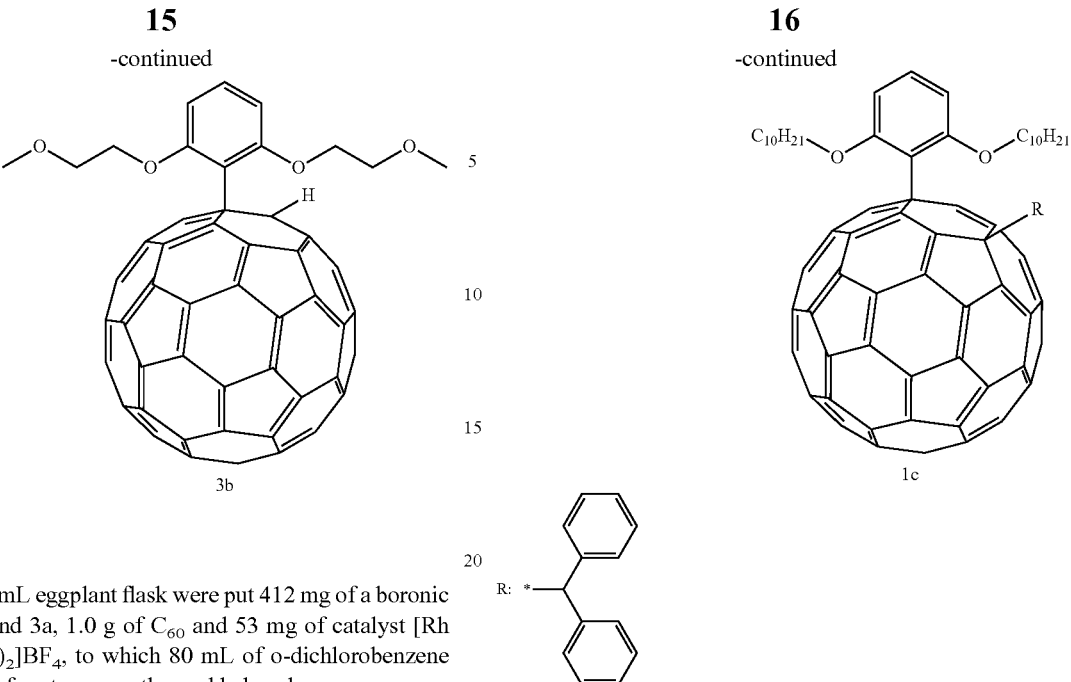

3b

Into a 200 mL eggplant flask were put 412 mg of a boronic acid compound 3a, 1.0 g of $C_{60}$ and 53 mg of catalyst [Rh(cod)(MeCN)$_2$]BF$_4$, to which 80 mL of o-dichlorobenzene and 20 mL of water were then added under an argon gas atmosphere, followed by stirring at 60° C. for 3 hours. After completion of the reaction, insolubles were filtered out and the solvent was removed under reduced pressure. The resulting product was separated and refined by recycle preparative column chromatography (toluene solvent) thereby producing 997 mg of 3b (yield 76%). The resulting product was confirmed with a high-performance liquid chromatography and identified with $^1$H-NMR, $^{13}$C-NMR, and MALDI-TOF-MS.

[Analyzed Data]

$^1$H-NMR (300 MHz; CDCl$_3$/CS$_2$) δ7.41 (t, 1H, 8.4 Hz), 6.89 (d, 2H, 8.4 Hz), 6.76 (s, 1H), 4.37 (br, 4H), 3.70 (t, 4H, 4.8 Hz), 3.26 (s, 6H); $^{13}$C-NMR (75 MHz; CDCl$_3$/CS$_2$) δ158.15, 155.91, 154.99, 147.29, 147.17, 147.05, 146.24, 146.11, 145.98, 145.87, 145.85, 145.18, 145.10, 144.95, 144.85, 144.61, 144.60, 143.27, 142.92, 142.42, 142.34, 142.12, 141.82, 141.58, 141.39, 141.37, 139.72, 139.03, 137.38, 135.41, 129.58 (CH), 122.98, 106.79 (CH), 70.37 (CH$_2$), 68.84 (CH$_2$), 63.57, 62.93 (CH), 58.79 (CH$_3$); MALDI-TOF-MS 946.0[M]$^+$.

Example 4

Synthesis of Fullerene Derivative 1c

Fullerene derivative 1c (BDP-DPM) was synthesized in the following manner.

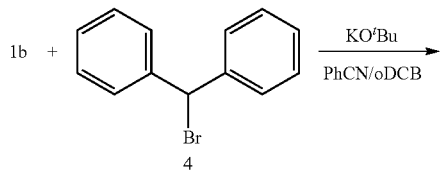

1c

R:

Into a 100 mL eggplant flask were put 100 mg of 1b synthesized in Example 1, to which 6 mL of o-dichlorobenzene and 12 mL of benzonitrile (PhCN) were then added under an argon gas atmosphere and 0.09 mL of potassium-tert-butoxide (1.0 M tetrahydrofuran solution) was added at 120° C., followed by stirring for one minute. To this solution was added 0.18 mL of a 0.5 M o-dichlorobenzene solution of a-bromodiphenyl methane 4, followed by stirring for 5 minutes. For this solution, filtration of insolubles and removal of the solvent were carried out, followed by separation and refining by recycle preparative GPC (solvent chloroform) thereby producing 55 mg of 1c (yield 50%). The resulting product was confirmed with a high-performance liquid chromatography and identified with $^1$H-NMR, $^{13}$C-NMR, and ESI-MS.

[Analyzed Data]

$^1$H-NMR (300 MHz; CD$_2$Cl$_2$) δ7.77 (d, 2H, 7.3 Hz), 7.69 (d, 2H, 7.3 Hz), 7.33 (t, 1H, 8.3 Hz), 7.24-7.19 (m, 4H), 7.14 (d, 2H, 7.2 Hz), 6.81 (d, 1H, 8.4 Hz), 6.68 (d, 1H, 8.4 Hz), 5.24 (s, 1H), 4.22 (t, 2H, 6.5 Hz), 3.93 (t, 2H, 5.8 Hz), 1.95-1.75 (m, 2H), 1.40 (br, 4H), 1.16 (br, 26H), 0.82-0.77 (m, 6H); $^{13}$C-NMR (75 MHz; CD$_2$Cl$_2$) δ160.13, 159.01, 156.75, 155.58, 154.13, 149.25, 149.16, 149.05, 149.01, 148.91, 148.84, 148.56, 148.35, 147.41, 147.35, 147.31, 147.25, 147.19, 147.05, 146.82, 146.66, 145.94, 145.70, 145.64, 145.53, 145.50, 145.45, 145.07, 145.03, 144.99, 144.66, 144.47, 144.44, 144.33, 144.21, 144.18, 144.04, 143.71, 143.61, 143.55, 143.41, 143.33, 143.28, 143.19, 143.16, 143.03, 142.96, 142.77, 142.74, 142.61, 142.27, 141.85, 141.59, 140.97, 140.58, 140.46, 140.24, 139.34, 138.94, 138.08, 130.86, 130.28 (CH), 129.93 (CH), 129.84 (CH), 128.68 (CH), 128.62 (CH), 128.15 (CH), 127.86 (CH), 127.72 (CH), 126.27 (CH), 116.05, 106.53 (CH), 106.20 (CH), 70.47 (OCH$_2$), 69.75 (OCH$_2$), 64.98 (CH), 63.86, 57.82, 32.29 (CH$_2$), 30.11 (CH$_2$), 30.03 (CH$_2$), 29.75 (CH$_2$), 29.30 (CH$_2$), 27.12 (CH$_2$), 27.04 (CH$_2$), 23.11 (CH$_2$), 14.33 (CH$_3$); ESI-MS 1300.4 [M+Na]$^+$.

Example 5

Synthesis of Fullerene Derivative 2c

Fullerene derivative 2c (BPP-DPM) was synthesized in the following manner.

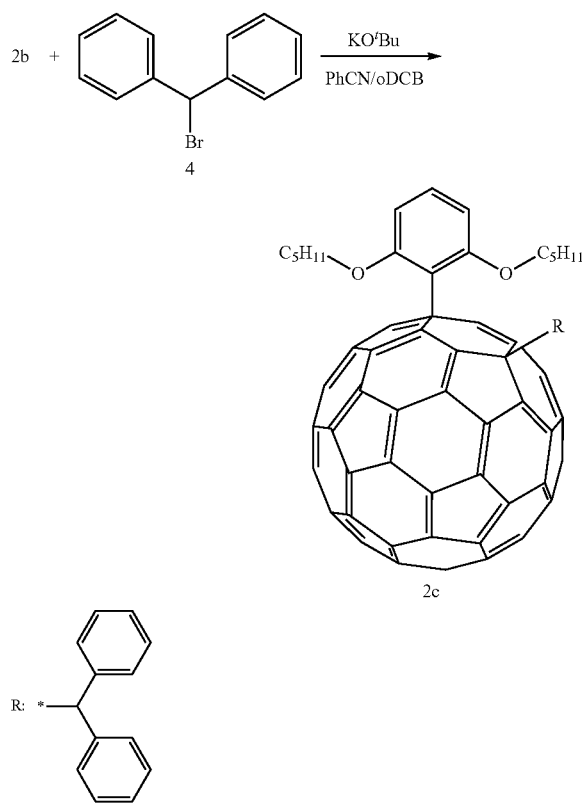

Into a 100 mL eggplant flask were put 250 mg of 2b synthesized in Example 2, to which 25 mL of o-dichlorobenzene and 25 mL of benzonitrile were added under an argon gas atmosphere and 0.26 mL of potassium-tert-butoxide (1.0 M tetrahydrofuran solution) was added at 120° C., followed by stirring for one minute. To this solution was added 0.51 mL of a 0.5 M o-dichlorobenzene solution of a-bromodiphenyl methane 4, followed by stirring for 5 minutes. For this solution, filtration of insolubles and removal of the solvent were carried out, followed by separation and refining by recycle preparative GPC (solvent chloroform) thereby producing 137 mg of 2c (yield 47%). The resulting product was confirmed with a high-performance liquid chromatography and identified with $^1$H-NMR, $^{13}$C-NMR, and ESI-MS.

[Analyzed Data]
$^1$H-NMR (270 MHz; CDCl$_3$) δ7.84 (d, 2H, 7.3 Hz), 7.74 (d, 2H, 7.3 Hz), 7.39 (t, 1H, 8.4 Hz), 7.31-7.21 (m, 6H), 6.86 (d, 1H, 8.2 Hz), 6.74 (d, 1H, 8.2 Hz), 5.28 (s, 1H), 4.29 (t, 2H, 6.6 Hz), 3.99 (t, 2H, 6.8 Hz), 1.94-1.82 (m, 2H), 1.50-1.21 (m, 10H), 0.91-0.80 (m, 6H); $^{13}$C-NMR (67.8 MHz; CDCl$_3$) δ159.74, 158.61, 156.21, 155.04, 153.61, 148.85, 148.68, 148.53, 148.10, 147.96, 147.06, 147.01, 146.98, 146.91, 146.84, 146.71, 146.21, 146.15, 145.73, 145.32, 145.17, 145.12, 144.70, 144.62, 144.30, 144.10, 143.91, 143.85, 143.80, 143.62, 143.34, 143.23, 143.00, 142.96, 142.85, 142.78, 142.68, 142.63, 142.44, 142.38, 142.27, 141.87, 141.48, 141.21, 140.47, 140.13, 140.06, 139.88, 138.98, 138.56, 137.65, 129.95 (CH), 129.60 (CH), 129.37 (CH), 128.26 (CH), 128.19 (CH), 127.42 (CH), 127.29 (CH), 115.9, 106.08 (CH), 105.76 (CH), 70.00 (CH$_2$), 69.28 (OCH$_2$), 64.61 (CH), 63.45, 57.32, 28.95 (CH$_2$), 28.72 (CH$_2$), 28.59 (CH$_2$), 28.47 (CH$_2$), 22.62 (CH$_2$), 14.11 (CH$_3$), 14.05 (CH$_3$); ESI-MS 1159.2 [M+Na]$^+$.

Example 6

Synthesis of Fullerene Derivative 3c

Fullerene derivative 3c (BMEP-DPM) was synthesized in the following manner.

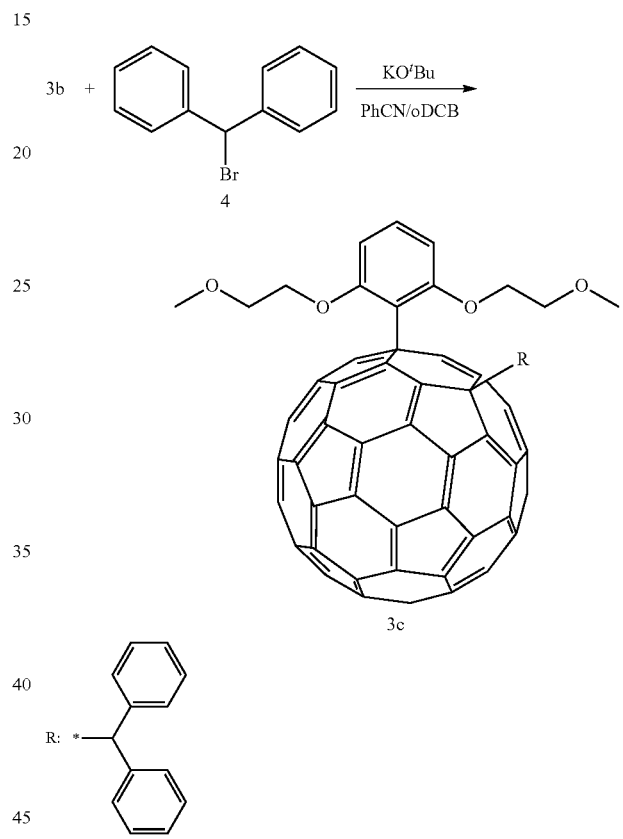

Into a 100 mL eggplant flask were put 200 mg of 3b synthesized in Example 3, to which 20 mL of o-dichlorobenzene and 20 mL of benzonitrile were then added under an argon gas atmosphere and 0.21 mL of potassium-tert-butoxide (1.0 M tetrahydrofuran solution) was added at 120° C., followed by stirring for one minute. To this solution was added 0.42 mL of a 0.5 M o-dichlorobenzene solution of a-bromodiphenyl methane 4, followed by stirring for 5 minutes. For this solution, filtration of insolubles and removal of the solvent were carried out, followed by separation and refining by recycle preparative GPC (solvent chloroform) thereby producing 118 mg of 3c (yield 50%). The resulting product was confirmed with a high-performance liquid chromatography and identified with $^1$H-NMR, $^{13}$C-NMR, and ESI-MS.

[Analyzed Data]
$^1$H-NMR (270 MHz; (CD$_3$)$_2$CO/CS$_2$) δ7.75 (d, 2H, 7.3 Hz), 7.65 (d, 2H, 7.3 Hz), 7.31 (t, 1H, 8.2 Hz), 7.22-7.04 (m, 6H), 6.81 (d, 1H, 8.2 Hz), 6.69 (d, 1H, 8.2 Hz), 5.19 (s, 1H), 4.33 (t, 2H, 4.8 Hz), 4.09-4.06 (m, 2H), 3.68 (t, 2H, 4.8 Hz), 3.35-3.26 (m, 2H), 3.22 (s, 3H), 3.15 (s, 3H); $^{13}$C-NMR (67.8 MHz; (CD$_3$)$_2$CO/CS$_2$) δ159.99, 158.47, 156.26, 155.74, 153.86, 149.13, 149.00, 148.95, 148.85, 148.73, 148.43, 148.32, 147.45, 147.37, 147.33, 147.24, 147.20, 147.07, 146.64, 146.30, 146.19, 145.72, 145.62, 145.50, 145.12, 145.03, 144.71, 144.52, 144.29, 144.16, 143.97, 143.73, 143.62, 143.41, 143.33, 143.17, 143.07, 142.78, 142.24, 141.98, 141.89, 141.60, 140.49, 140.40, 140.11, 140.07, 139.56, 138.98, 138.24, 130.46 (CH), 130.16 (CH), 129.88 (CH), 128.67 (CH), 128.54 (CH), 128.08 (CH), 127.84 (CH), 127.68 (CH), 116.56, 107.13 (CH), 106.73 (CH), 71.06 (OCH$_2$), 70.64 (OCH$_2$), 69.26 (OCH$_2$), 68.98 (OCH$_2$), 64.76 (CH), 63.82, 59.19 (OCH$_3$), 57.47; ESI-MS 1135.2 [M+Na]$^+$.

Example 7

Synthesis of Fullerene Derivative 1d

Fullerene derivative 1d (BDP-Bn) was synthesized in the following manner.

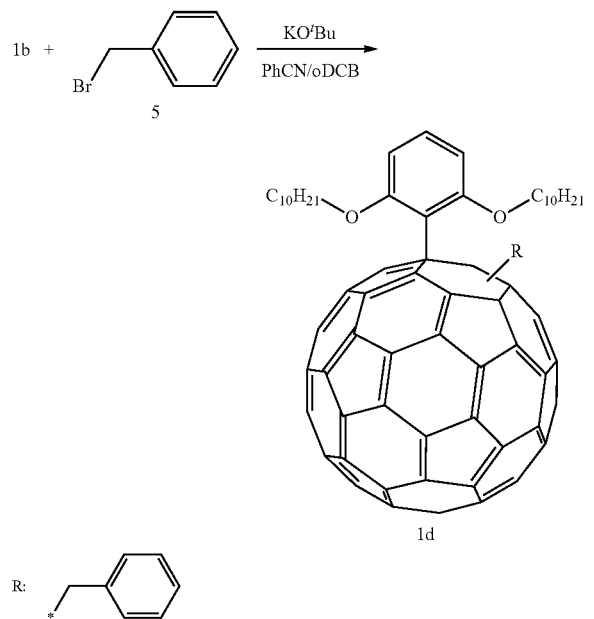

1d

Into a 100 mL eggplant flask were put 100 mg of 1b synthesized in Example 1, to which 1 mL of o-dichlorobenzene, 8 mL of benzonitrile and 0.21 mL of benzylbromide 5 were then added under an argon gas atmosphere and 0.54 mL of potassium-tert-butoxide (0.25 M 1-methyl-2-pyrrolidone solution) was added at room temperature, followed by stirring for 30 minutes. After insolubles were filtered out, the solvent was removed, followed by separation and refining by recycle preparative GPC (solvent chloroform) thereby producing 50 mg of 1d (yield 46%). The resulting product was confirmed with a high-performance liquid chromatography and identified with $^1$H-NMR, $^{13}$C-NMR, and FD-MS.

[Analyzed Data]
$^1$H-NMR (270 MHz; CD$_2$Cl$_2$) δ7.46-6.73 (m, 8H), 4.35 (s, 2H), 4.32-4.03 (m, 4H), 2.0 1-0.91 (m, 2H), 1.73-1.63 (m, 2H), 1.59-1.15 (m, 28H), 0.77 (t, 6H, 6.3 Hz); $^{13}$C-NMR (67.8 MHz; CD$_2$Cl$_2$) δ159.71, 158.66, 157.95, 156.87, 154.49, 149.07, 148.78, 148.64, 148.46, 147.95, 147.45, 147.30, 147.20, 147.03, 146.85, 146.65, 146.48, 146.40, 146.21, 145.82, 145.75, 145.57, 145.41, 145.32, 145.23, 145.18, 144.62, 144.53, 144.44, 144.30, 144.24, 143.87, 143.74, 143.51, 143.25, 143.14, 143.00, 142.84, 142.76, 142.72, 142.50, 142.42, 141.98, 141.81, 141.69, 141.52, 141.16, 139.30, 139.24, 138.53, 138.40, 138.33, 137.60, 137.13, 136.62, 132.53 (CH), 130.96 (CH), 130.53 (CH), 129.8 (CH), 128.29 (CH), 128.07 (CH), 127.57 (CH), 127.05 (CH), 119.30, 116.42, 1106.43 (CH), 106.12 (CH), 70.12 (OCH$_2$), 69.58, 68.55, 60.24, 57.77, 48.63 (Bn-CH$_2$), 47.94 (Bn-CH$_2$), 32.28 (CH$_2$), 30.16 (CH$_2$), 30.12 (CH$_2$), 30.06 (CH$_2$), 30.01 (CH$_2$), 29.98 (CH$_2$), 29.84 (CH$_2$), 29.76 (CH$_2$), 29.73 (CH$_2$), 29.63 (CH$_2$), 27.43 (CH$_2$), 27.09 (CH$_2$), 23.09 (CH$_2$), 14.28 (CH$_3$); FD-MS 1201.8 [M]

Example 8

Synthesis of Fullerene Derivative 1e

Fullerene derivative 1e (BDP-Hex) was synthesized in the following manner.

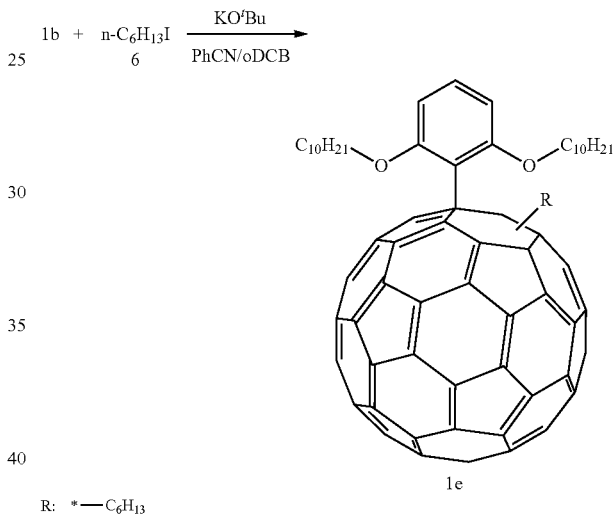

1e

Into a 100 mL eggplant flask were put 100 mg of 1b synthesized in Example 1, to which 20 mL of benzonitrile and 0.27 mL of 1-iodinehexane 6 were then added under an argon gas atmosphere and 0.54 mL of potassium-tert-butoxide (0.25 M tetrahydrofuran solution) was added at room temperature, followed by stirring for 30 minutes. After insolubles were filtered out, the solvent was removed, followed by separation and refining by recycle preparative GPC (solvent chloroform) thereby producing 59 mg of 1e (yield 55%). The resulting product was confirmed with a high-performance liquid chromatography and identified with $^1$H-NMR, $^{13}$C-NMR, and FD-MS.

[Analyzed Data]
$^1$H-NMR (270 MHz; CD$_2$Cl$_2$) δ7.38-7.32 (m, 1H), 6.8 3-6.74 (m, 2H), 4.2 3-4.13 (m, 4H), 3.15-3.09 (m, 1H), 2.8 3-2.80 (m, 1H), 2.08-1.14 (br, 40H), 0.8 3-0.74 (m, 9H); $^{13}$C-NMR (67.8 MHz; CD$_2$Cl$_2$) δ160.09, 159.55, 159.09, 159.02, 156.95, 154.42, 149.10, 149.06, 148.84, 148.79, 148.73, 148.60, 148.46, 148.04, 147.47, 147.38, 147.26, 147.17, 146.98, 146.90, 146.82, 146.67, 146.49, 146.39, 146.25, 146.04, 145.81, 145.78, 145.61, 145.56, 145.47, 145.37, 145.29, 145.24, 145.02, 144.60, 144.55, 144.51, 144.38, 144.23, 144.15, 143.83, 143.74, 143.50, 143.33, 143.29, 143.26, 143.19, 143.15, 143.02, 142.86, 142.75, 142.70, 142.54, 142.03, 141.89, 141.76, 141.66, 141.44, 140.45, 140.04, 139.51, 139.24, 138.71, 138.40, 137.19, 136.99, 130.3 (CH), 129.88 (CH), 119.40, 116.86, 106.33 (CH), 106.16 (CH), 70.06 ($OCH_2$), 68.29, 68.22, 59.71, 57.86, 42.47 ($CH_2$), 42.30 ($CH_2$), 32.29 ($CH_2$), 30.31 ($CH_2$), 30.12 ($CH_2$), 30.08 ($CH_2$), 29.98 ($CH_2$), 29.95 ($CH_2$), 29.83 ($CH_2$), 29.75 ($CH_2$), 29.62 ($CH_2$), 27.51 ($CH_2$), 27.38 ($CH_2$), 27.07 ($CH_2$), 23.09 ($CH_2$), 23.01 ($CH_2$), 22.95 ($CH_2$), 14.31 ($CH_3$); FD-MS 1195.8$[M]^+$.

Example 9

Synthesis of Fullerene Derivative 7b

Fullerene derivative 7b (bis-HpTMP $C_{60}$) was synthesized in the following manner.

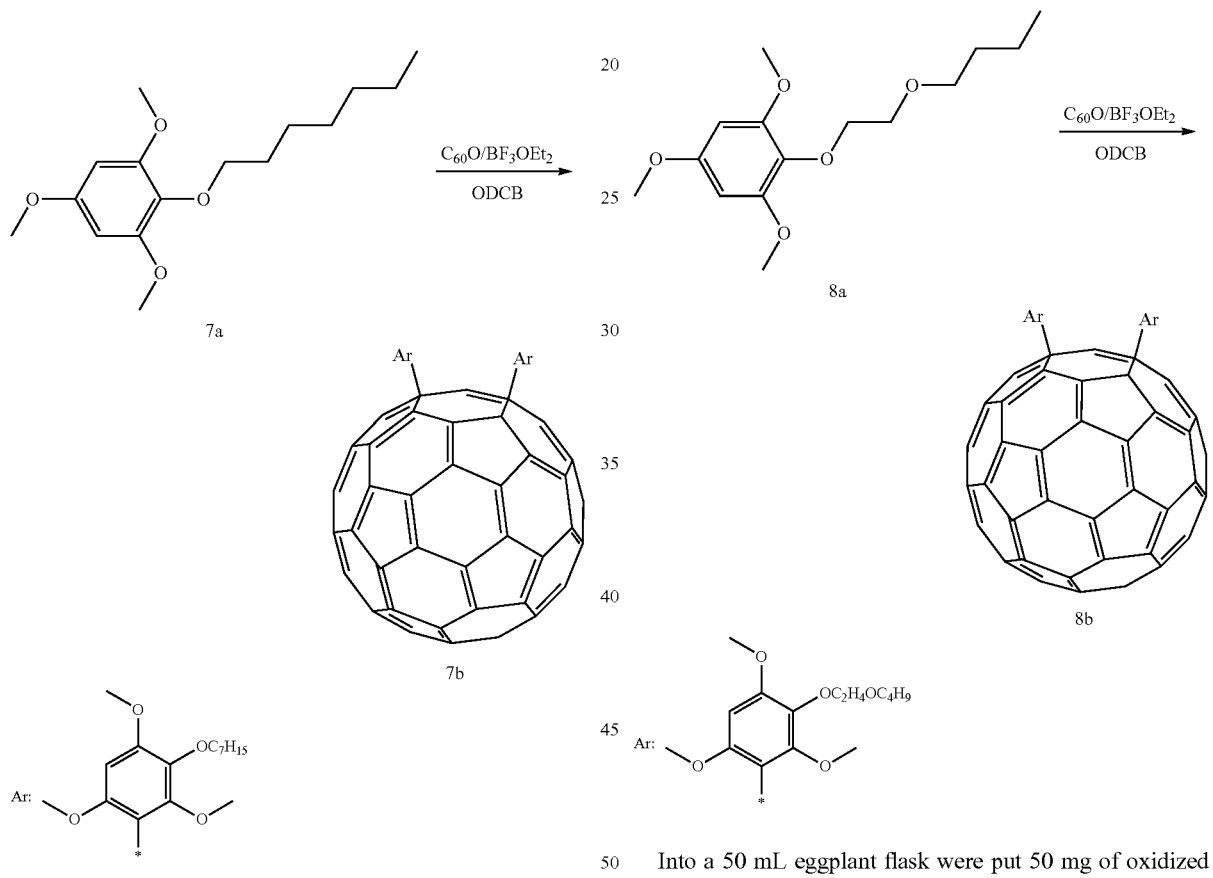

Into a 50 mL eggplant flask were put 40 mg of oxidized fullerene ($C_{60}O$) and 153 mg of 7a, to which 8 mL of o-dichlorobenzene were then added under an argon gas atmosphere and 34 μL of trifluoroborane diethylether complex at 0° C., followed by stirring for 3.5 hours. After insolubles were filtered out, the solvent was removed. The resulting produce was washed with acetone and methanol and then separated and refined by recycle preparative GPC (solvent chloroform) thereby producing 30 mg of 7b (yield 44%). The resulting product was confirmed with a high-performance liquid chromatography and identified with $^1$H-NMR, $^{13}$C-NMR, and MALDI-TOF-MS.

[Analyzed Data]
$^1$H-NMR (300 MHz; $CDCl_3$) δ6.39 (s, 1H), 3.91 (s, 3H), 3.86 (t, 2H, 6.7 Hz), 3.83 (s, 3H), 3.76 (s, 3H), 1.75 (m, 2H), 1.49-1.25 (m, 8H), 0.90 (t, 3H, 6.7 Hz); $^{13}$C-NMR (75.5 MHz; $CDCl_3$) δ155.65, 154.98, 153.95, 153.68, 150.17, 148.67, 148.55, 148.25, 147.02, 146.92, 146.65, 145.27, 145.05, 144.59, 144.18, 144.00, 143.65, 143.59, 143.28, 142.93, 142.84, 142.73, 142.46, 142.38, 141.30, 140.48, 140.20, 139.09, 137.34, 136.54, 114.89, 93.29 (CH), 73.67 ($OCH_2$), 60.86 ($OCH_3$), 56.41, 55.99 ($OCH_3$), 55.77 ($OCH_3$), 31.90 ($CH_2$), 30.34 ($CH_2$), 29.21 ($CH_2$), 26.07 ($CH_2$), 22.66 ($CH_2$), 14.13 ($CH_3$); MALDI-TOF-MS 1282.3$[M]^+$.

Example 10

Synthesis of Fullerene Derivative 8b

Fullerene derivative 8b (bis-BETMP $C_{60}$) was synthesized in the following manner.

Into a 50 mL eggplant flask were put 50 mg of oxidized fullerene and 193 mg of 8a, to which 10 mL of o-dichlorobenzene were then added under an argon gas atmosphere and 43 μL of trifluoro borane diethyl ether complex were added at 0° C., followed by stirring for 3.5 hours. After insolubles were filtered out, the solvent was removed. The product was washed with acetone and methanol and then separated and refined by recycle preparative GPC (solvent chloroform) thereby producing 32 mg of 8b (yield 37%). The resulting product was confirmed by high-performance liquid chromatography and identified with $^1$H-NMR, $^{13}$C-NMR, and MALDI-TOF-MS.

[Analyzed Data]
$^1$H-NMR (270 MHz; $CDCl_3$) δ6.39 (s, 1H), 4.04 (t, 2H, 4.6 Hz), 3.92 (s, 3H), 3.83 (s, 3H), 3.79 (s, 3H), 3.72 (t, 2H, 4.7 Hz), 3.52 (t, 2H, 6.6 Hz), 1.6 (m, 2H), 1.39 (m, 2H), 0.92 (t, 3H, 7.3 Hz); $^{13}$C-NMR (67.8 MHz; $CDCl_3$) δ155.79, 154.92, 153.90, 153.60, 150.08, 148.65, 148.51, 148.16, 146.97, 146.87, 146.61, 145.24, 145.00, 144.55, 144.17, 143.96, 143.60, 143.54, 143.24, 142.89, 142.79, 142.69, 142.41, 142.33, 141.28, 140.43, 139.12, 137.31, 136.09, 114.75, 93.14 (CH), 72.32 ($OCH_2$), 71.10 ($OCH_2$), 70.00 ($OCH_2$), 60.93 ($OCH_3$), 56.33, 56.00 ($OCH_3$), 55.65 ($OCH_3$), 31.84 ($CH_2$), 19.32 ($CH_2$), 13.97 ($CH_3$); MALDI-TOF-MS 1286.3 $[M]^+$.

Example 11

Measurement of First Reduction Potential

A solution for the measurement was prepared by adding 3.87 mg of ferrocene to 50 mL of a 0.1 M o-dichlorobenzene solution of a tetrabutylammonium perchloric acid salt. To 2 mL of this solution was added 1.5 mg of a fullerene derivative to measure the oxidation-reduction potential at a sweep rate 20 mV/s with an electrochemical analyzer model 630A manufactured by ALS. The first reduction potential (mV) was set forth in Table 1. As shown in Table 1, the fullerene derivatives exhibited a larger first reduction potential than the conventional fullerene derivative (PCBM).

TABLE 1

First Reduction Potential of Fullerene Derivatives (mV; FC/FC+ basis)

| Compound No. | Fullerene Derivative | First Redution Potential (mV; FC/FC$^+$ basis) |
|---|---|---|
| 1b | BDP-H | 1245 |
| 1c | BDP-DPM | 1259 |
| 2c | DPP-DPM | 1254 |
| 3c | BMEP-DPM | 1258 |
| 7b | bis-HpTMPC$_{60}$ | 1293 |
| 8b | bis-BETMPC$_{60}$ | 1291 |
|  | PCBM | 1153 |

Example 12

Manufacturing of Organic Photoelectric Conversion Device

Baytron P (manufactured by H.C. Stark GmbH) was spin-coated at 5000 rpm (50s) on a glass substrate having been washed, on which an ITO film with a surface resistance of 15 Ω/sq was formed by sputtering, and then dried at a temperature of 200° C. for 10 minutes. Fullerene derivative 1c was mixed with poly(3-hexylthiophene) having a molecular weight of 17,500 (manufactured by Sigma-Aldrich Co. LLC) at a weight ratio of 1.0:0.5, and then dissolved in chlorobenzene such that the concentration of fullerene derivative 1c was one percent by weight. This mixed solution was spin-coated on the glass substrate at 1000 rpm (50 s) thereby forming a photoelectric conversion layer. The ITO-glass substrate with the photoelectric conversion layer was heated under a nitrogen atmosphere at 150° C. for 6 minutes and then titanium tetraisopropoxide was spin-coated at 4000 rpm over the substrate and left for 30 minutes. A 100 nm thickness Al was deposited under a vacuum of about $10^{-5}$ torr to form a counter electrode thereby producing a photoelectric conversion device. While an artificial sunlight of 100 mW/cm$^2$ was irradiated to the photoelectric conversion device, the voltage-current characteristics thereof were measured. The maximum efficiency was calculated from the voltage-current characteristics.

Example 13

A photoelectric conversion device was produced using 2c in place of 1c in the same manner as Example 12 to measure the voltage-current characteristics, from which the maximum efficiency was calculated.

Example 14

A photoelectric conversion device was produced using 3c in place of 1c in the same manner as Example 12 to measure the voltage-current characteristics, from which the maximum efficiency was calculated.

Example 15

A photoelectric conversion device was produced using 1d in place of 1c in the same manner as Example 12 to measure the voltage-current characteristics, from which the maximum efficiency was calculated.

Example 16

A photoelectric conversion device was produced using 1e in place of 1d in the same manner as Example 12 to measure the voltage-current characteristics, from which the maximum efficiency was calculated.

The results of Examples 12 to 16 are set forth in Table 2

TABLE 2

Photoelectric Conversion Characteristics of Fullerene Derivatives

| Compound No. | Fullerene Derivative | $J_{sc}$ [mA/cm$^2$] | $V_{oc}$ [V] | FF | Efficiency [%] |
|---|---|---|---|---|---|
| 1c | BDP-DPM | 3.93 | 0.51 | 0.35 | 0.7 |
| 2c | BPP-DPM | 1.24 | 0.41 | 0.35 | 0.18 |
| 3c | BMEP-DPM | 2.18 | 0.44 | 0.28 | 0.27 |
| 1d | BDP-Bn | 4.73 | 0.56 | 0.36 | 0.95 |
| 1e | BDP-Hex | 1.96 | 0.47 | 0.36 | 0.33 |

Applicability In Industry

The fullerene derivative of the present invention is an organic semiconductor material, which can be used in an organic TFT and an organic solar cell and is significantly large in industrial value.

The invention claimed is:

1. A fullerene derivative represented by formula (I):

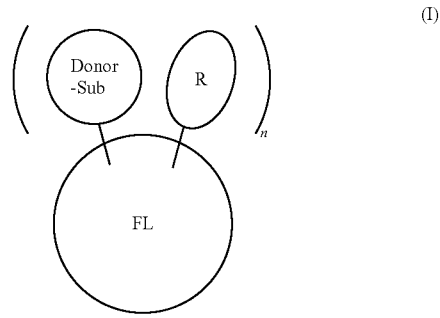

(I)

wherein the encircled FL represents fullerene $C_{60}$ or $C_{70}$, Donor-Sub represents a substituent having a structure shown below, R is selected from hydrogen, Donor-Sub, alkyl, cycloalkyl, alkoxy, alkoxy-substituted alkyl, alkoxy-substituted alkoxy, alkylthio-substituted alkoxy, alkylthio, alkylthio-substituted alkylthio, and alkoxy-substituted alkylthio groups, each having a total carbon atoms of 1 to 20, benzyl and phenyl groups, and n is an integer of 1 to 10:

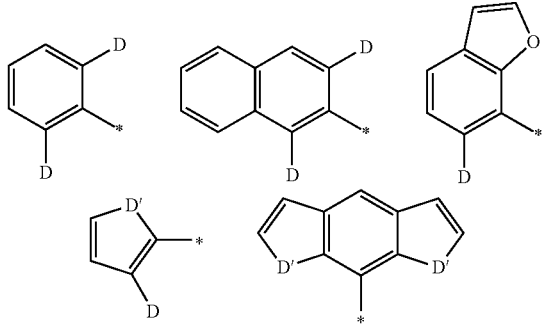

$D = OR^1, NR^1{}_2, SR^1$
$D' = O, S$ wherein $R^1$ is selected from alkyl, cycloalkyl, alkoxy, alkoxy-substituted alkyl, alkoxy-substituted alkoxy, alkylthio-substituted alkoxy, alkylthio, alkylthio-substituted alkylthio, and alkoxy-substituted alkylthio groups, each having a total carbon atoms of 1 to 20, benzyl and phenyl groups and contains an unsaturated bond or a branched structure.

2. The fullerene derivative according to claim 1 having a first reduction potential of 1245 mV or higher.

3. A photoelectric conversion device having a heterojunction layer comprising a p type conjugate polymer having electron donating properties and an n type fullerene derivative, wherein the fullerene derivative according to claim 1 is used in a photoelectric conversion layer.

4. A photoelectric conversion device having a heterojunction layer comprising a p type conjugate polymer having electron donating properties and an n type fullerene derivative, wherein the fullerene derivative according to claim 2 is used in a photoelectric conversion layer.

* * * * *